(12) United States Patent
Barry

(10) Patent No.: US 11,040,079 B2
(45) Date of Patent: *Jun. 22, 2021

(54) **COMPOSITIONS DERIVED FROM *GALENIA AFRICANA* AND METHODS OF USE FOR CANCER TREATMENT**

(71) Applicant: BIOPHARM NZ LIMITED, Hamilton (NZ)

(72) Inventor: Michael-John Joseph Barry, Hamilton (NZ)

(73) Assignee: BIOPHARM NZ LIMITED, Whitiora Hamilton (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 16/472,690

(22) PCT Filed: Dec. 19, 2017

(86) PCT No.: PCT/IB2017/058097
§ 371 (c)(1),
(2) Date: Jun. 21, 2019

(87) PCT Pub. No.: WO2018/116146
PCT Pub. Date: Jun. 28, 2018

(65) Prior Publication Data
US 2019/0365840 A1  Dec. 5, 2019

(30) Foreign Application Priority Data
Dec. 21, 2016 (ZA) .................. 2016/08789

(51) Int. Cl.
*A61K 36/185* (2006.01)
*A61K 36/36* (2006.01)
*A61P 35/00* (2006.01)
*A61K 31/353* (2006.01)
*A61K 45/06* (2006.01)

(52) U.S. Cl.
CPC ............ *A61K 36/36* (2013.01); *A61K 31/353* (2013.01); *A61P 35/00* (2018.01); *A61K 45/06* (2013.01)

(58) Field of Classification Search
CPC .................................................. A61K 36/185
See application file for complete search history.

(56) References Cited

PUBLICATIONS

Mativandlela et al., "Antimycobacterial flavonoids from the leaf extract of Galenia africana," J Nat Prod 72:2169-2171, 2009.*

TESS record for U.S. Trademark Reg. No. 2,864,342, Colonial Chemical Co., 2004.*
International Search Report dated Feb. 21, 2018 in corresponding International Application No. PCT/IB2017/058097.
Benguedouar, et al, "Ethanolic Extract of Algerian Propolis and Galangin Decreased Murine Melanoma T", 2016, pp. 1172-1183, vol. 16, No. 9, Anti-Cancer Agents in Medicinal Chemistry.
Tan, et al, "Identification of novel dietary phytochemicals inhibiting the efflux transporter breast cancer resistance protein (BCRP/ABCG2)", Jun. 15, 2013, pp. 2267-2274, vol. 138, No. 4, Food Chemistry.
Awasthi, et al, "Molecular docking and 3D-QSAR-based virtual screen of flavonoids as potential aromatase inhibitors against estrogen-dependent breast cancer", 2015, pp. 804-819, vol. 33, No. 4, Journal of Biomolecular Structure and Dynamics.
Lou, et al, "2',4'-Dihydroxychalcone-induced apoptosis of human gastric cancer MGC-803 cells via down-regulation of surviving mRNA", 2010, pp. 1333-1337, vol. 24, Toxicology in Vitro.
Rasul, et al., "Pinocembrin: A Novel Natural Compound with Versatile Pharmacological and Biological Activities", 2013, 10 pages, vol. 2013, BioMed Research International.
Kumar, et al, "Pinocembrin triggers Bax-dependent mitochondrial apoptosis in colin cancer cells", Dec. 21, 2006, pp. 231-241, vol. 46, No. 3, Molecular Carcinogenesis.
Ticha, et al, "Phytochemical and Antimicrobial Screening of Flavanones and Chalcones from Galenia Africana and Dicerothamnus rhinocerotis", 2015, pp. 1185-1190, vol. 10, 7, Natural Product Communications.
Chen, et al, "Pinocembrin suppresses TGR-β1-induced epithelial-mesenchymal transition and metastasis of human Y-79 retinoblastoma cells through inactivating ανβα signaling pathway", 2014, 14 pages, vol. 4, No. 41, Cell & Bioscience.
Zaki, et al, Bioactive Formylated Flavonoids from Eugenia rigida: Isolation, Synthesis, and X-ray Crystallography, Sep. 2016, 2341-2349, vol. 79, Journal of Natural Products.
Ghani, et al, "Chemical Constituents and Cytotoxic Activity of *Polyalthia cauliflora* var. cauliflora", 2012, pp. 74-82, vol. 6, No. 1, Research Journal of Medicinal Plant.
Yang, et al, "Antimetastatic potentials of flavones on oral cancer cell via an inhibition of matrix-degrading proteases", Mar. 2008, pp. 287-294, vol. 53, No. 3, Archives of Oral Biology.
Mativandlela, et al, "Antimycobacterial Flavonoids from the Leaf Extract of Galenia africana", 2009, pp. 2169-2171, vol. 72, No. 12, J. Nat. Prod.
Chen, et al., "Antiproliferative and apoptotic effects of pinocembrin in human prostate cancer cells", 2013, pp. 255-262, vol. 8, No. 3, Bangladesh Journal of Pharmacology.

\* cited by examiner

*Primary Examiner* — Rosanne Kosson
(74) *Attorney, Agent, or Firm* — Stephen J. Weyer, Esq.; Stites & Harbison, PLLC

(57) ABSTRACT

The present invention discloses a cancer treatment method which includes the step of treating a patient having cancer with an extract from *Galenia Africana* L. plant. The extract may include pinocembrin and/or 2',4' dihydroxychalcone and/or 7-hydroxyflavanone. The cancer may be breast cancer or melanoma. The composition may be solubilized with MPG and/or Suganate.

8 Claims, 8 Drawing Sheets

MCF-7 human breast cancer cells treated with GA extracts (MTT Assay 1)

MCF-7 human breast cancer cells treated with GA extracts (Cell Titer Glo Assay)

COMPOSITIONS DERIVED FROM *GALENIA AFRICANA* AND METHODS OF USE FOR CANCER TREATMENT

FIELD OF INVENTION

The present invention relates to a cancer treatment method and composition.

More particularly, the present invention relates to a cancer treatment method and composition for treating breast cancer and melanoma.

BACKGROUND TO INVENTION

Kraalbos (KB) extracts from *Galenia Africana* L. plant are known to be rich in pinocembrin, 2',4' dihydroxychalcone, 7-hydroxyflavanone and 2',4' dihydroxydihydrochalcone compounds. These molecules have previously been shown to exhibit varying degrees of cytotoxity on cancer cells.

It is an object of the invention to suggest a novel cancer treatment method and composition which includes an extract of *Galenia Africana*.

SUMMARY OF INVENTION

According to the invention, a cancer treatment method includes the steps of treating a patient having cancer with an extract from *Galenia Africana* L. plant.

Also according to the invention, a cancer treatment composition includes an extract from *Galenia Africana* L. plant.

The extract may include pinocembrin and/or 2',4' dihydroxychalcone and/or 7-hydroxyflavanone.

The cancer may be breast cancer.

The cancer may be melanoma.

The composition may be solubilized.

The composition may be solubilized with MPG and/or Suganate.

BRIEF DESCRIPTION OF THE DRAWINGS

The invention will now be described with reference to the figures as follows.

DETAILED DESCRIPTION OF INVENTION

The invention will now be described by way of example.

According to the invention, a cancer treatment method includes the steps of treating a patient having cancer with an extract from *Galenia Africana* L. plant.

Also according to the invention, a cancer treatment composition includes an extract from *Galenia Africana* L. plant.

The extract may include pinocembrin and/or 2',4' dihydroxychalcone and/or 7-hydroxyflavanone.

The cancer may be breast cancer.

The cancer may be melanoma.

The composition may be solubilized.

The composition may be solubilized with MPG and/or Suganate.

Experiment 1

The objective of the experiment was to test the role of *Galenia Africana* (GA) extracts on the proliferation of MCF-7 human breast cancer cells. Cells were treated with B1, B2, B3, D1, D1B2 or D1B3. D1 exhibited the most cytotoxicity (IC50 of 26.53 μg/ml), followed by B2 (IC50 of 32.28 μg/ml). Based on the chemical composition of these extracts, it is clear that those that contain high levels of 2',4' dihydroxychalcone have the most effect. Indeed, a combination of D1 and B3 at 50:50 ratio had minimal effect as compared to a combination of D1 and B2 at 70:30 ratio.

Figure 1:
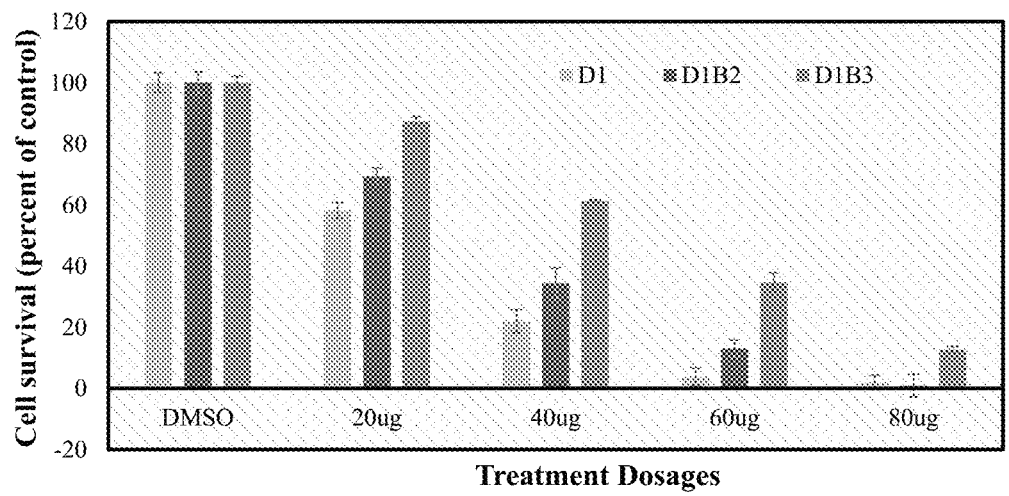
FIG. 1 is a graph for MCF-7 human breast cancer cells treated with GA extract fractionates (8-16-16-repeat) comparing cell survival (percent of control) versus treatment dosages.
Figure 2:
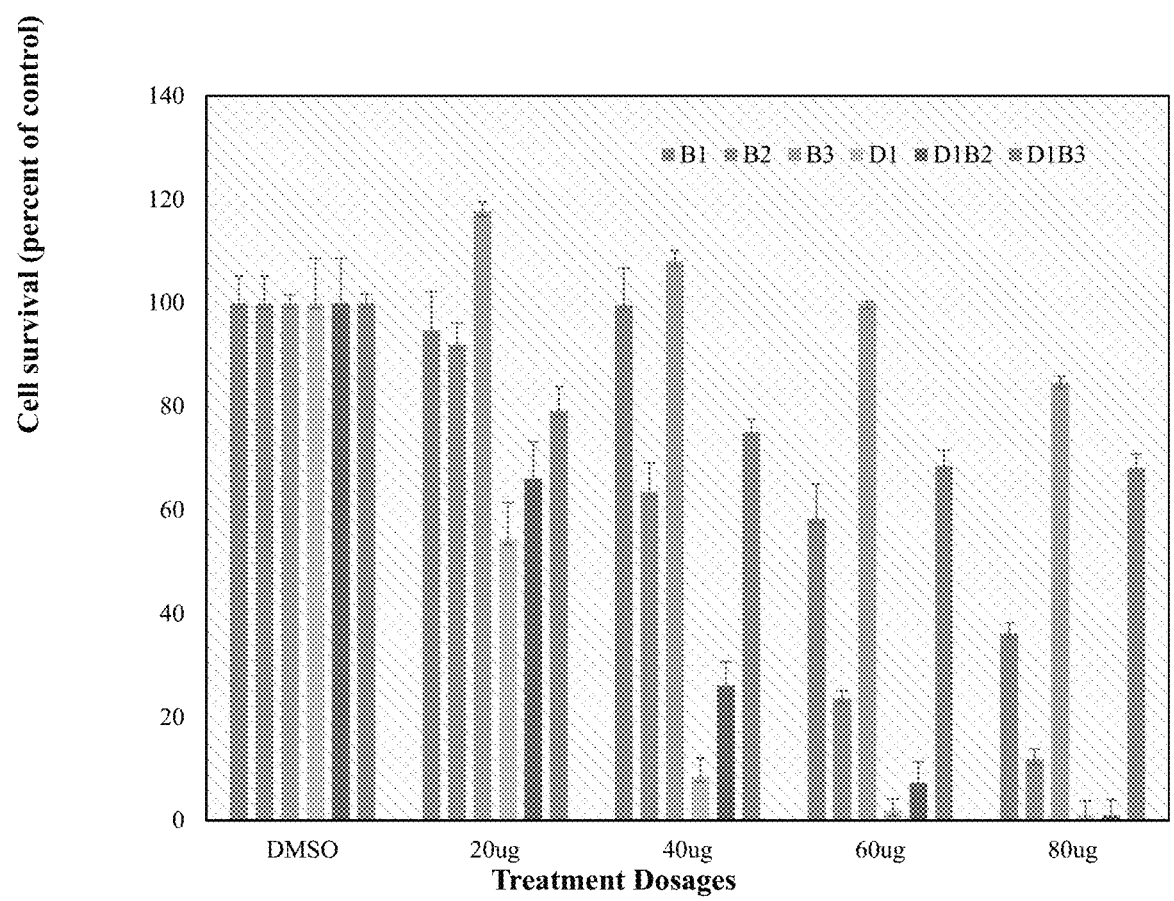
FIG. 2 is a graph for MCF-7 human breast cancer cells treated with GA extract fractionates comparing cell survival (percent of control) with treatment dosages.

The results are shown in FIGS. 1 and 2.

TABLE 1

IC50s of GA extracts on MCF-7 human breast cancer cells

| | |
|---|---|
| B1 | 73.84 μg/ml |
| B2 | 46.68 μg/ml |
| D1 | 26.53 μg/ml |
| D1B2 | 32.28 μg/ml |

TABLE 2

Chemical compositions of GA extracts with emphasis on pinocembrin and 2',4' dihydroxychalcone

| Items, % | pinocembrin | 2',4'-dihydroxychalcone |
|---|---|---|
| B1 | 20.46 | 14.95 |
| B2 | 40.86 | 42.97 |
| B3 | 90.09 | 1.38 |
| D1 | | 75 |

Experiment 2

The objective of the experiment was to test the role of *Galenia Africana* extracts on the proliferation of MCF-7 human breast cancer cells.

Figure 3:
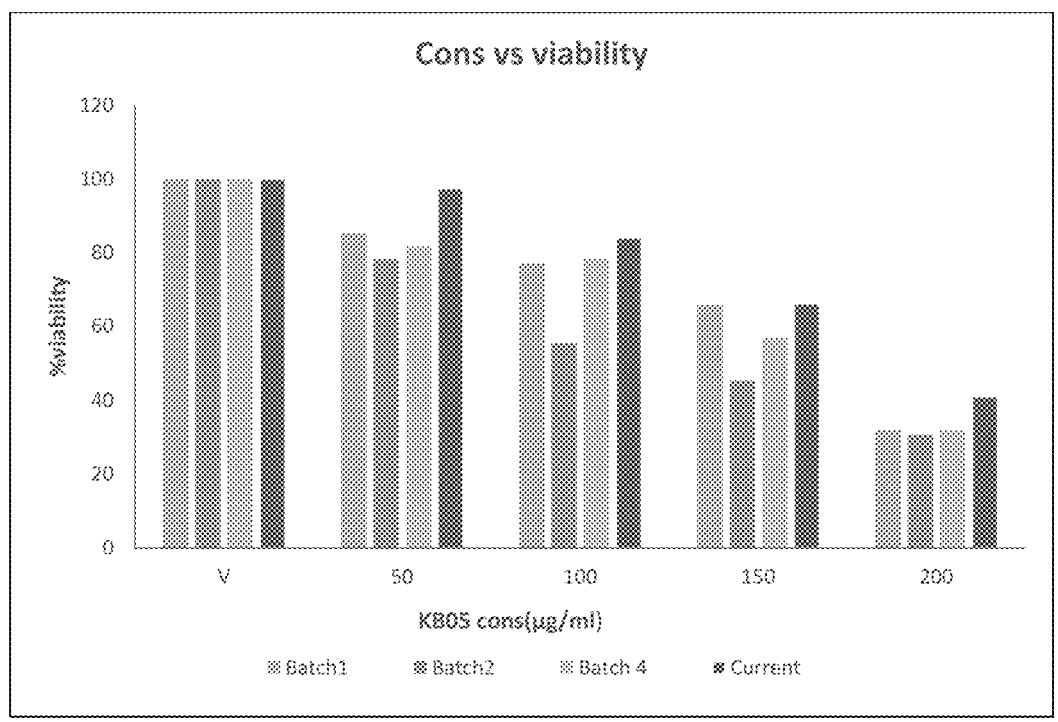
FIG. 3 is a graph for MCF-7 human breast cancer cells treated with GA extracts (MTT Assay 1) comparing percent viability with KB05 concentration (μg/ml).
Figure 4:
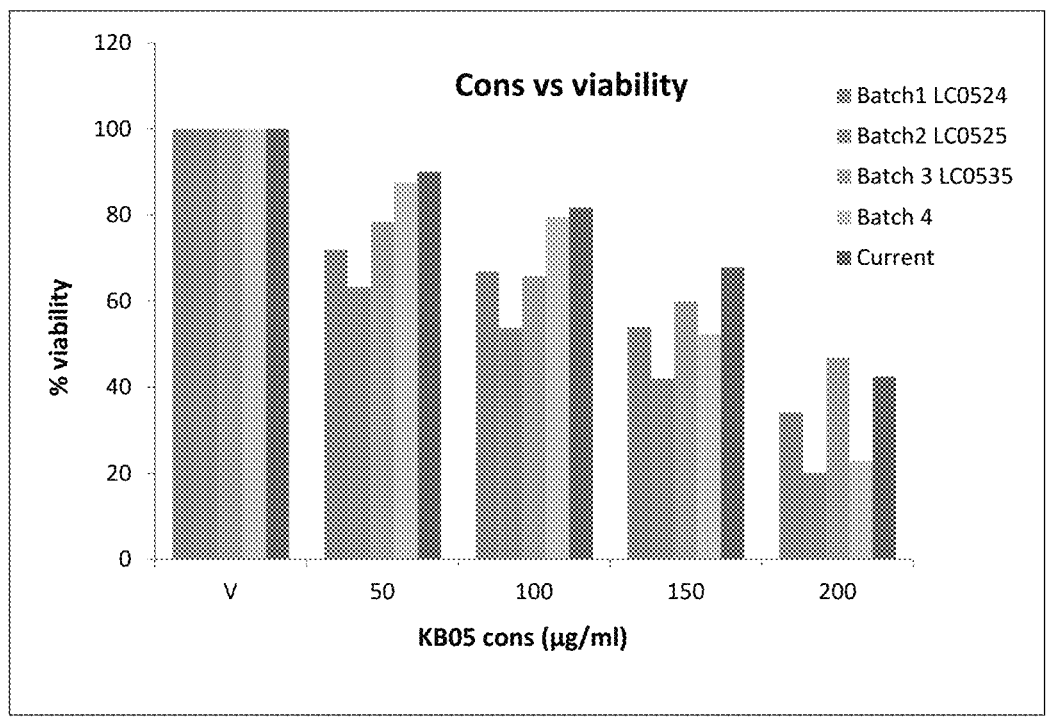
FIG. 4 is a graph of MCF-7 human cancer breast cells treated with GA extracts (MTT Assay 2) comparing percent viability with K605 concentration (μg/ml).
Figure 5:
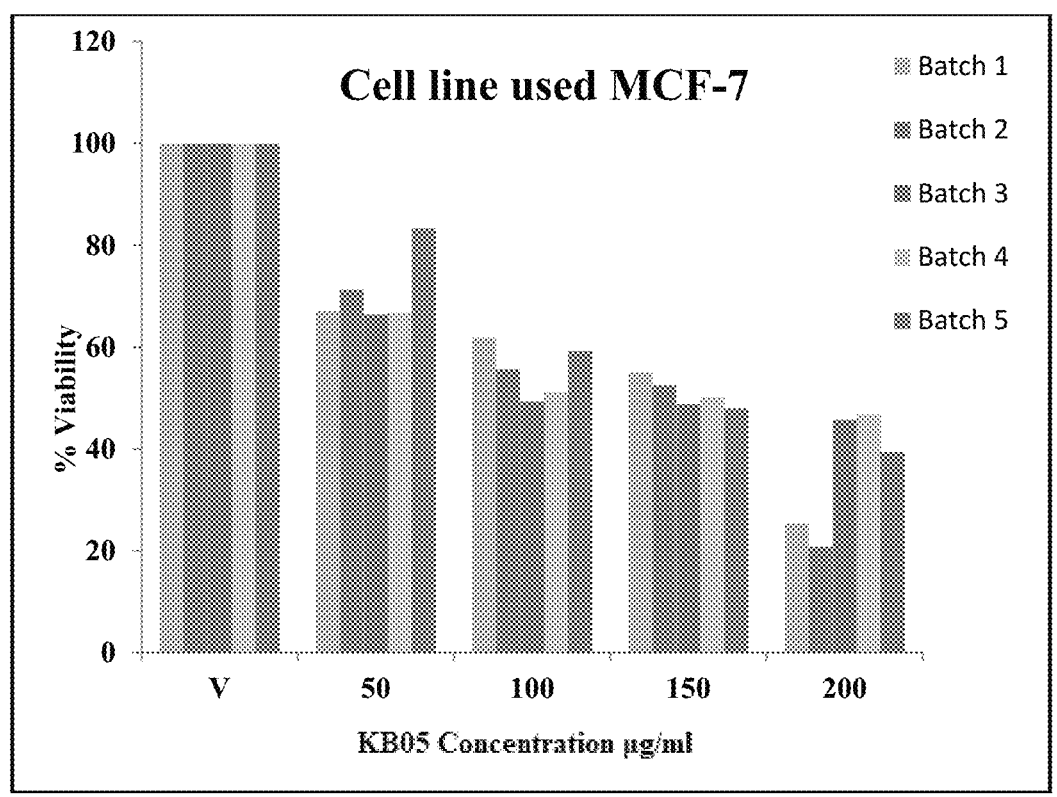
FIG. 5 is a graph for MCF-7 human breast cancer cells treated with GA extracts (Cell Titer Glo Assay) comparing percent viability with K605 concentration (μg/ml).
Figure 6:
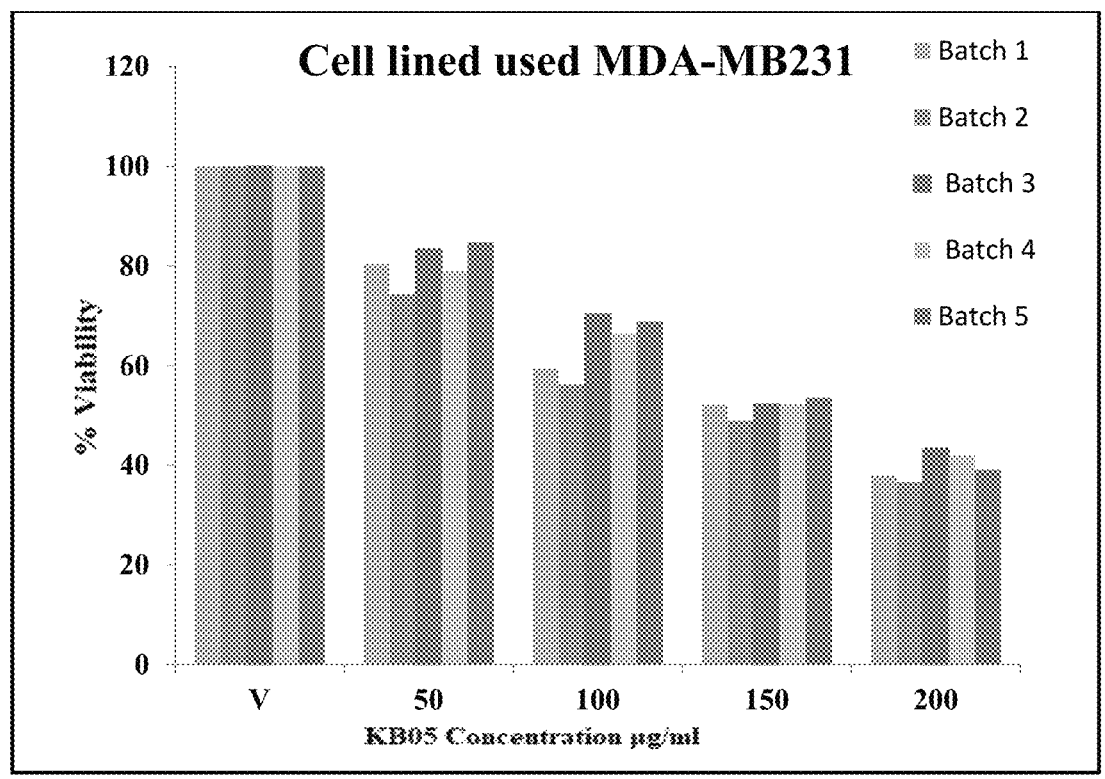
FIG. 6 is a graph for MDA-MB231 human breast cancer cells treated with GA extracts (Cell Titer Glo Assay) comparing percent viability with KB05 concentration (μg/ml).

The results are shown in FIGS. 3 and 4.

| Chemical compositions of GA extracts | | | | |
|---|---|---|---|---|
| Batches | 7-hydroxyflavanone | pinocembrin | 2',4'-dihydroxychalcone | 2',4'-dihydroxydihydrochalcone |
| LC0524(1) | 3.3% | 9.6% | 7.6% | 3.1% |
| LC0525(2) | 3.0% | 8.4% | 6.8% | 2.8% |
| LC0535(3) | 2.4% | 4.3% | 3.4% | 0.7% |
| Batch 4 | 2.4% | 12.4% | 8.9% | 3.2% |

| Batches | IC50 value (µg/mL) |
|---|---|
| LC0524(1) | 146.0 |
| LC0525(2) | 93.39 |
| LC0535(3) | 195.6 |
| Batch 4 | 148.1 |
| Current | 187.1 |

| Batches | IC50 value (µg/mL) |
|---|---|
| LC0524(1) | 124.2 |
| LC0525(2) | 114 |
| LC0535(3) | 132 |
| Batch 4 | 144.1 |
| Batch 5 | 141.6 |

| Batches | IC50 value (µg/mL) |
|---|---|
| LC0524(1) | 144.2 |
| LC0525(2) | 130.5 |
| LC0535(3) | 166.3 |
| Batch 4 | 160.8 |
| Batch 5 | 158.4 |

Figure 7:
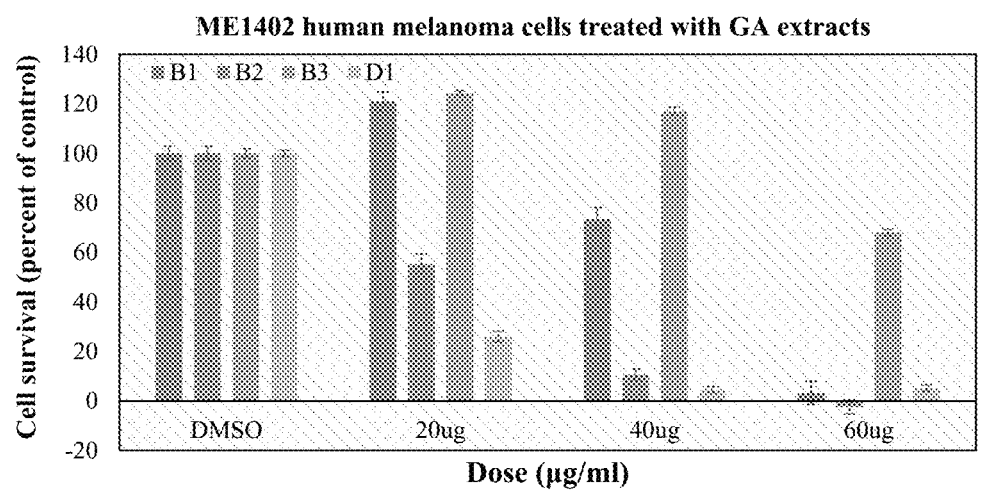
FIG. 7 is a graph for ME1402 human melanoma cells treated with GA extracts comparing survival with dosage.

FIG. 7 depicts ME1402 human melanoma cells treated with GA extracts after 48 hrs of incubation. Mean cell survival calculated as percentage of the mean vehicle control.

Figure 8:
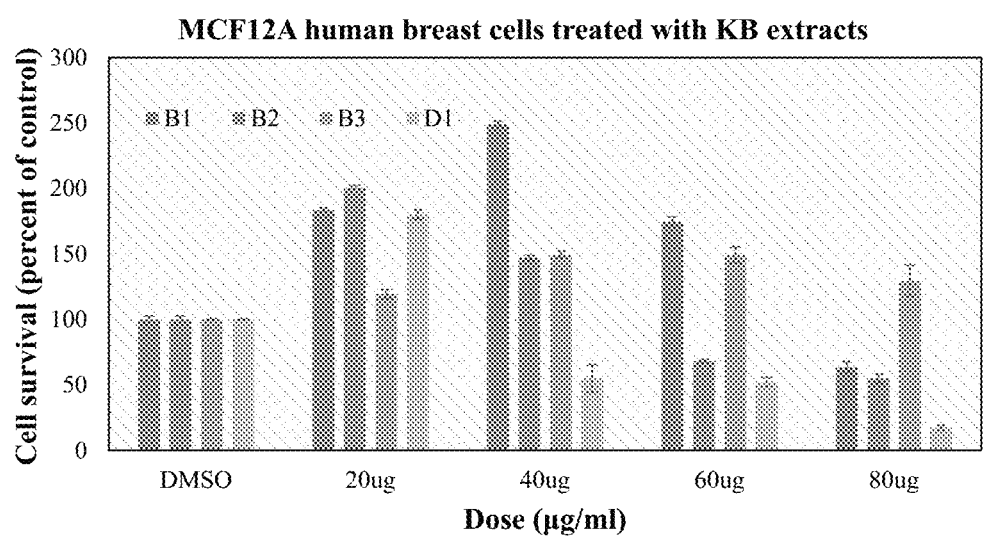
FIG. 8 is a graph for MCF12A human breast cells treated with KB extracts comparing cell survival with dosage.

FIG. 8 depicts MCF12A human breast cells treated with KB extracts after 48 hrs of incubation. Mean cell survival calculated as percentage of the mean vehicle control.

The invention claimed is:

1. A cancer treatment composition which includes a therapeutically effective amount of an extract from the plant *Galenia africana*, wherein the extract is solubilized with mono-propylene glycol (MPG) and/or sodium laurylglucosides hydroxypropylsulfonate.

2. The composition as claimed in claim 1, in which the extract includes pinocembrin and/or 2',4' dihydroxychalcone and/or 7-hydroxyflavanone.

3. The composition as claimed in claim 1, in which the cancer is breast cancer.

4. The composition as claimed in claim 1, in which the cancer is melanoma.

5. A method of treating cancer in a patient in need thereof, comprising administering to the patent a therapeutically effective amount of the composition of claim 1.

6. The method as claimed in claim 5, in which the extract includes pinocembrin and/or 2', 4' dihydroxychalcone and/or 7-hydroxyflavanone.

7. The method as claimed in claim 5, in which the cancer is breast cancer.

8. The method as claimed in claim 5, in which the cancer is melanoma.

\* \* \* \* \*